United States Patent
Guevremont et al.

(10) Patent No.: US 7,034,289 B2
(45) Date of Patent: Apr. 25, 2006

(54) SEGMENTED SIDE-TO-SIDE FAIMS

(75) Inventors: Roger Guevremont, Ottawa (CA); Randy Purves, Orleans (CA); David Barnett, Orleans (CA)

(73) Assignee: Ionalytics Corporation, Ottawa (CA)

( * ) Notice: Subject to any disclaimer, the term of this patent is extended or adjusted under 35 U.S.C. 154(b) by 56 days.

(21) Appl. No.: 10/503,714

(22) PCT Filed: Feb. 7, 2003

(86) PCT No.: PCT/CA03/00169

§ 371 (c)(1),
(2), (4) Date: Aug. 6, 2004

(87) PCT Pub. No.: WO03/067236

PCT Pub. Date: Aug. 14, 2003

(65) Prior Publication Data

US 2005/0151072 A1  Jul. 14, 2005

Related U.S. Application Data

(60) Provisional application No. 60/354,711, filed on Feb. 8, 2002.

(51) Int. Cl.
*H01J 49/00* (2006.01)
*B01D 59/44* (2006.01)

(52) U.S. Cl. .................. 250/288; 250/281; 250/282; 250/286; 250/291

(58) Field of Classification Search .................. None
See application file for complete search history.

(56) References Cited

U.S. PATENT DOCUMENTS 4,855,595 A  8/1989  Blanchard (Continued)

FOREIGN PATENT DOCUMENTS

| WO | WO 00/63949 | 10/2000 |
|---|---|---|
| WO | WO 03/067625 | 8/2003 |
| WO | WO 2004/030129 A2 | 4/2004 |

OTHER PUBLICATIONS

Buryakov et al., "A New Method of Separation of Multi-Atomic Ions by Mobility at Atmospheric Pressure using a High-Frequency Amplitude-Asymmetric Strong Electric Field", Int. J. Mass Spectrom. Ion Processes, No. 128, pp. 143-148, (1993), Elsevier Science Publishers B.V.

(Continued)

*Primary Examiner*—Nikita Wells
(74) *Attorney, Agent, or Firm*—Freedman & Associates

(57) ABSTRACT

Provided is a side-to-side high field asymmetric waveform ion mobility spectrometer (FAIMS) including a generally cylindrically-shaped inner electrode having a length. Encircling the inner electrode is a generally cylindrically-shaped outer electrode assembly comprising at least first and second and third outer electrode segments. Each of the outer electrode segments has a channel extending therethrough and open at opposite ends thereof. In an assembled condition, the second outer electrode segment is disposed intermediate the first and third outer electrode segments in an end-to-end arrangement, each one of the first and second and third electrode segments overlapping a different portion of the length of the inner electrode. An electrical contact is provided on at least one of the inner electrode and the second outer electrode segment for receiving a first direct current voltage between the inner electrode and the second outer electrode segment, and for applying an asymmetric waveform voltage to the at least one of the inner electrode and the second outer electrode segment. The second outer electrode segment is maintained at a different potential relative to the first and third outer electrode segments, such that a potential gradient is formed in a direction along the length of the inner electrode.

23 Claims, 6 Drawing Sheets

U.S. PATENT DOCUMENTS

| | | | |
|---|---|---|---|
| 5,420,424 | A | 5/1995 | Carnahan et al. |
| 5,789,745 | A | 8/1998 | Martin et al. |
| 5,847,386 | A | 12/1998 | Thomson et al. |
| 5,905,258 | A | 5/1999 | Clemmer |
| 6,111,250 | A | 8/2000 | Thomson et al. |
| 6,124,592 | A | 9/2000 | Spangler |
| 6,495,823 | B1 | 12/2002 | Miller et al. |
| 6,512,224 | B1 | 1/2003 | Miller et al. |
| 6,559,441 | B1 | 5/2003 | Clemmer |
| 6,621,077 | B1 * | 9/2003 | Guevremont et al. ....... 250/292 |
| 6,690,004 | B1 | 2/2004 | Miller et al. |
| 6,753,522 | B1 * | 6/2004 | Guevremont et al. ....... 250/287 |
| 2001/0030285 | A1 | 10/2001 | Miller et al. |
| 2003/0089847 | A1 | 5/2003 | Guevremont et al. |
| 2003/0213899 | A9 | 11/2003 | Guevremont et al. |

OTHER PUBLICATIONS

Eiceman et al., "Ion Mobility Spectrometry", (1994), CRC Press, Florida.

Carnahan et al., "Field Ion Spectrometry—A New Analytical Technology for Trace Gas Analysis", Proceedings of the 41st Annual ISA Analysis Division Symposium, paper #96-009, pp. 87-95, (1996), Framingham, MA, USA.

Purves et al., "Mass Spectrometric Characterization of a High-Field Asymmetric Waveform Ion Mobility Spectrometer", Review of Scientific Instruments, vol. 69, No. 12, pp. 4094-4105, (Dec. 1998), American Institute of Physics.

Henderson et al., "ESI/Ion Trap/Ion Mobility/Time-of-Flight Mass Spectrometry for Rapid and Sensitive Analysis of Biomolecular Mixtures", Anal. Chem. 1999, vol. 71, No. 2, pp. 291-301, (Jan. 15, 1999), American Chemical Society.

Guevremont et al., "Atmospheric Pressure Ion Focusing in a High-Field Asymmetric Waveform Ion Mobility Spectrometer", Review of Scientific Instruments, vol. 70, No. 2, pp. 1370-1383, (Feb. 1999), American Institute of Physics.

Krylov, "A Method of Reducing Diffusion Losses in a Drift Spectrometer", Tech. Phys., vol. 44, No. 1, pp. 113-116, (1999), American Institute of Physics.

* cited by examiner

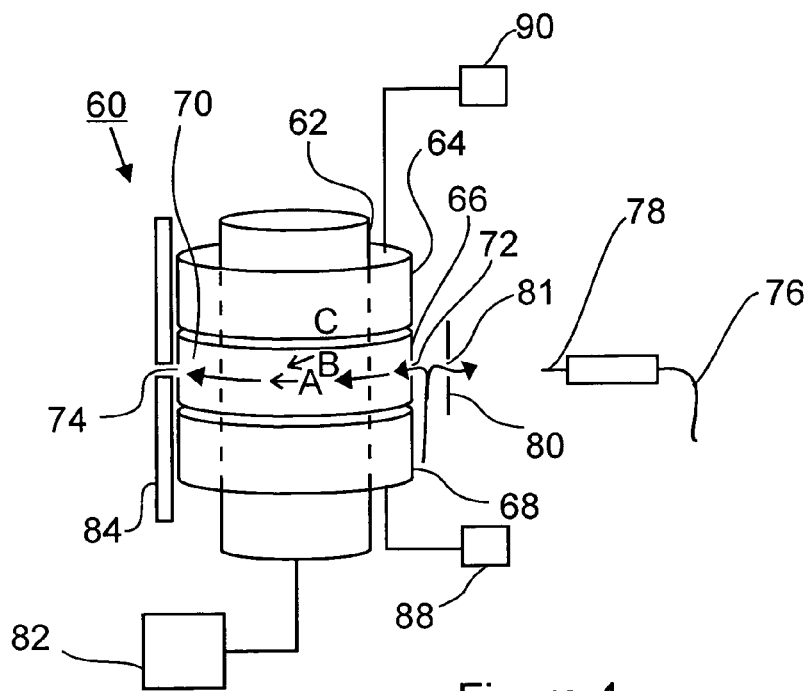
Figure 4
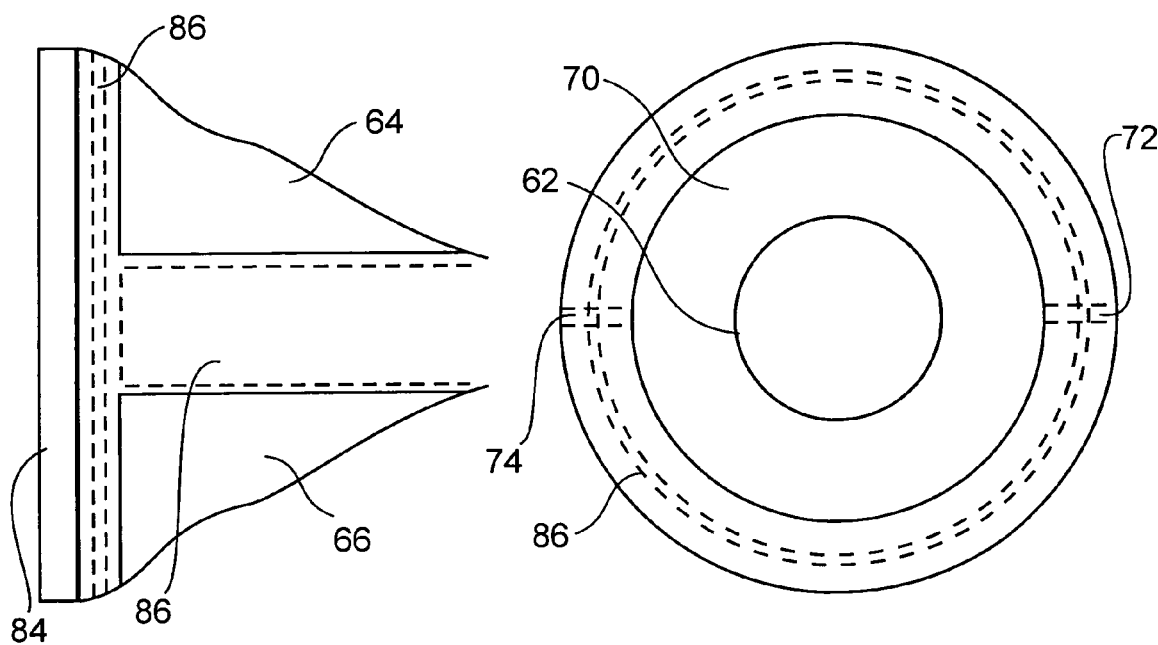
Figure 5
Figure 6

US 7,034,289 B2

SEGMENTED SIDE-TO-SIDE FAIMS

This application claims the benefit of U.S. Provisional Application No. 60/354,711 filed Feb. 8, 2002.

FIELD OF THE INVENTION

The instant invention relates generally to high field asymmetric waveform ion mobility spectrometry (FAIMS), more particularly the instant invention relates to a side-to-side FAIMS having a generally cylindrical inner electrode and a multi-segmented generally cylindrical outer electrode assembly.

BACKGROUND OF THE INVENTION

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994). In IMS, gas-phase ion mobilities are determined using a drift tube with a constant electric field. Ions are separated in the drift tube on the basis of differences in their drift velocities. At low electric field strength, for example 200 V/cm, the drift velocity of an ion is proportional to the applied electric field strength, and the mobility, K, which is determined from experimentation, is independent of the applied electric field. Additionally, in IMS the ions travel through a bath gas that is at sufficiently high pressure that the ions rapidly reach constant velocity when driven by the force of an electric field that is constant both in time and location. This is to be clearly distinguished from those techniques, most of which are related to mass spectrometry, in which the gas pressure is sufficiently low that, if under the influence of a constant electric field, the ions continue to accelerate.

E. A. Mason and E. W. McDaniel in their book entitled "Transport Properties of Ions in Gases" (Wiley, New York, 1988) teach that at high electric field strength, for instance fields stronger than approximately 5,000 V/cm, the ion drift velocity is no longer directly proportional to the applied electric field, and K is better represented by $K_H$, a non-constant high field mobility term. The dependence of $K_H$ on the applied electric field has been the basis for the development of high field asymmetric waveform ion mobility spectrometry (FAIMS). Ions are separated in FAIMS on the basis of a difference in the mobility of an ion at high field strength, $K_H$, relative to the mobility of the ion at low field strength, K. In other words, the ions are separated due to the compound dependent behavior of $K_H$ as a function of the applied electric field strength.

In general, a device for separating ions according to the FAIMS principle, has an analyzer region that is defined by a space between first and second spaced-apart electrodes. The first electrode is maintained at a selected dc voltage, often at ground potential, while the second electrode has an asymmetric waveform V(t) applied to it. The asymmetric waveform V(t) is composed of a repeating pattern including a high voltage component, $V_H$, lasting for a short period of time $t_H$ and a lower voltage component, $V_L$, of opposite polarity, lasting a longer period of time $t_L$. The waveform is synthesized such that the integrated voltage-time product, and thus the field-time product, applied to the second electrode during each complete cycle of the waveform is zero, for instance $V_H t_H + V_L t_L = 0$; for example +2000 V for 10 μs followed by −1000 V for 20 μs. The peak voltage during the shorter, high voltage portion of the waveform is called the "dispersion voltage" or DV, which is identically referred to as the applied asymmetric waveform voltage.

Generally, the ions that are to be separated are entrained in a stream of gas flowing through the FAIMS analyzer region, for example between a pair of horizontally oriented, spaced-apart electrodes. Accordingly, the net motion of an ion within the analyzer region is the sum of a horizontal x-axis component due to the stream of gas and a transverse y-axis component due to the applied electric field. During the high voltage portion of the waveform an ion moves with a y-axis velocity component given by $v_H = K_H E_H$, where $E_H$ is the applied field, and $K_H$ is the high field ion mobility under operating electric field, pressure and temperature conditions. The distance traveled by the ion during the high voltage portion of the waveform is given by $d_H = v_H t_H = K_H E_H t_H$, where $t_H$ is the time period of the applied high voltage. During the longer duration, opposite polarity, low voltage portion of the asymmetric waveform, the y-axis velocity component of the ion is $v_L = K E_L$, where K is the low field ion mobility under operating pressure and temperature conditions. The distance traveled is $d_L = v_L t_L = K E_L t_L$. Since the asymmetric waveform ensures that $(V_H t_H) + (V_L t_L) = 0$, the field-time products $E_H t_H$ and $E_L t_L$ are equal in magnitude. Thus, if $K_H$ and K are identical, $d_H$ and $d_L$ are equal, and the ion is returned to its original position along the y-axis during the negative cycle of the waveform. If at $E_H$ the mobility $K_H > K$, the ion experiences a net displacement from its original position relative to the y-axis. For example, if a positive ion travels farther during the positive portion of the waveform, for instance $d_H > d_L$, then the ion migrates away from the second electrode and eventually will be neutralized at the first electrode.

In order to reverse the transverse drift of the positive ion in the above example, a constant negative dc voltage is applied to the second electrode. The difference between the dc voltage that is applied to the first electrode and the dc voltage that is applied to the second electrode is called the "compensation voltage" (CV). The CV voltage prevents the ion from migrating toward either the second or the first electrode. If ions derived from two compounds respond differently to the applied high strength electric fields, the ratio of $K_H$ to K may be different for each compound. Consequently, the magnitude of the CV that is necessary to prevent the drift of the ion toward either electrode is also different for each compound. Thus, when a mixture including several species of ions, each with a unique $K_H/K$ ratio, is being analyzed by FAIMS, only one species of ion is selectively transmitted to a detector for a given combination of CV and DV. In one type of FAIMS experiment, the applied CV is scanned with time, for instance the CV is slowly ramped or optionally the CV is stepped from one voltage to a next voltage, and a resulting intensity of transmitted ions is measured. In this way a CV spectrum showing the total ion current as a function of CV, is obtained.

Guevremont et al. have described the use of curved electrode bodies, for instance inner and outer cylindrical electrodes, for producing a two-dimensional atmospheric pressure ion focusing effect that results in higher ion transmission efficiencies than can be obtained using, for example, a FAIMS device having parallel plate electrodes. In particular, with the application of an appropriate combination of DV and CV an ion of interest is focused into a band-like region in the annular gap between the cylindrical electrodes as a result of the electric fields which change with radial distance. Focusing the ions of interest has the effect of reducing the number of ions of interest that are lost as a result of the ion suffering a collision with one of the inner and outer electrodes. FAIMS devices with cylindrical electrode geometry have been described in the prior art, as for example in U.S. Pat. No. 5,420,424, the contents of which are incorporated herein by reference.

In WO 00/08455, the contents of which are incorporated herein by reference, Guevremont and Purves describe a domed-FAIMS analyzer. In particular, the domed-FAIMS analyzer includes a cylindrical inner electrode having a curved surface terminus proximate an ion outlet orifice of the FAIMS analyzer region. The curved surface terminus is substantially continuous with the cylindrical shape of the inner electrode and is aligned co-axially with the ion outlet orifice. During use, the application of an asymmetric waveform to the inner electrode results in the normal ion-focusing behavior as described above, and in addition the ion-focusing action extends around the generally spherically shaped terminus of the inner electrode. This causes the selectively transmitted ions to be directed generally radially inwardly within the region that is proximate the terminus of the inner electrode. Several contradictory forces are acting on the ions in this region near the terminus of the inner electrode. The force of the carrier gas flow tends to influence the ions to travel towards the ion-outlet orifice, which advantageously also prevents the ions from migrating in a reverse direction, back towards the ion source. Additionally, the ions that get too close to the inner electrode are pushed back away from the inner electrode, and those near the outer electrode migrate back towards the inner electrode, due to the focusing action of the applied electric fields. When all forces acting upon the ions are balanced, the ions are effectively captured in every direction, either by forces of the flowing gas, or by the focusing effect of the electric fields of the FAIMS mechanism. This is an example of a three-dimensional atmospheric pressure ion trap, as described in greater detail by Guevremont and Purves in WO 00/08457, the contents of which are incorporated herein by reference.

Guevremont and Purves further disclose a near-trapping mode of operation for the above-mentioned domed-FAIMS analyzer, which achieves ion transmission from the domed-PAIMS to a mass spectrometer with high efficiency. Under near-trapping conditions, the ions that accumulate in the three-dimensional region of space near the spherical terminus of the inner electrode are caused to leak from this region, being pulled by a flow of gas towards the ion-outlet orifice. The ions that are extracted from this region do so as a narrow, approximately collimated beam, which is pulled by the gas flow through the ion-outlet orifice and into a smaller orifice leading into the vacuum system of the mass spectrometer. Accordingly, a tandem domed-FAIMS/MS device is a highly sensitive instrument that is capable of detecting and identifying ions of interest at part-per-billion levels.

More recently, in WO 01/69216 the contents of which is incorporated herein by reference, Guevremont and Purves describe a so-called "perpendicular-gas-flow-FAIMS", which is identically referred to as a side-to-side FAIMS. The analyzer region of the side-to-side FAIMS is defined by an annular space between inner and outer cylindrical electrodes. In particular, ions that are introduced into the analyzer region of the side-to-side FAIMS are selectively transmitted in a direction that is generally around the circumference of the inner electrode. For instance, the ion inlet and the ion outlet of a side-to-side FAIMS device are disposed, one opposing the other, within a surface of the outer electrode such that ions are selectively transmitted through the curved analyzer region between the ion inlet and the ion outlet along a continuously curving ion flow path absent a portion having a substantially linear component. In particular, the ions travel from the ion inlet to the ion outlet by flowing around the inner electrode in one of a "clockwise" and a "counter clock-wise" direction. This is in contrast to the above-mentioned FAIMS devices in which the ions are selectively transmitted along the length of the inner electrode.

Advantageously, the side-to-side FAIMS device reduces the minimum distance that must be traveled by the ions within the analyzer region to approximately fifty percent of the circumference of the inner electrode. Since the ions split into two streams traveling in opposite directions around the inner electrode after they are introduced through the ion inlet, the effective ion density within the analyzer region is reduced, and so too is the ion-ion repulsion space charge effect reduced. Furthermore, the reduction of the minimum ion travel distance has the added benefit of improving the ion transmission efficiency. For example, by keeping the time for travel short, the effect of diffusion and ion-ion repulsion forces are minimized. In keeping distances short, the transit time of the ions through the analyzer region is also short, which supports more rapid analysis of ion mixtures.

Of course, the side-to-side FAIMS device also has some limitations. For example, ion separation occurs only within a very small portion of the analyzer region of a side-to-side FAIMS. With only two possible ion flow directions through the analyzer region, the ion concentration at a point along either ion flow direction remains relatively high. As the ions transit the analyzer region, diffusion and ion-ion repulsion forces, even though they are small, cause the ions to spread out in a direction along the length of the inner and outer electrodes. Accordingly, the ions are introduced through the ion inlet as an approximately collimated beam of ions, but rapidly spread out to form a sheet of ions that travels around the inner electrode to the ion outlet. Furthermore, ions are focused between the inner and outer electrodes as a result of the application of the applied CV and DV, but this focusing occurs only in a direction that is approximately normal to the electrode surfaces, i.e. in a radial direction. As such, there is no force capable of focusing the ions in a direction that is parallel to the electrode surfaces, i.e. in a longitudinal direction. Since the ions spread out slightly during separation, some of the ions become entrained in portions of the analyzer region where the gas flow rate is low or stagnant. Consequently the ion transmission efficiency from the FAIMS to, for example, an external mass spectrometer is reduced.

Additionally, the strength of the focusing field between the inner and outer electrodes is related to the radius of the cylindrically shaped inner electrode. In order to produce stronger focusing fields, it is necessary to utilize an inner electrode with a smaller radius. Of course, a FAIMS analyzer having a smaller inner electrode also has a smaller available volume for separating ions. The distance between the ion inlet orifice and the ion outlet orifice is also smaller, and may result in insufficient ion transit times to effect separation of a mixture that contains different ionic species having similar high field ion mobility properties.

It would be advantageous to provide a FAIMS apparatus including a detection system that overcomes the limitations of the prior art.

SUMMARY OF THE INVENTION

In accordance with the invention there is provided an apparatus for separating ions, comprising: an inner electrode assembly comprising at least an inner electrode segment, the at least an inner electrode segment having a length and a curved outer surface in a direction transverse to its length and an outer electrode assembly comprising at least an outer electrode segment, the at least an outer electrode segment having a length, a channel extending through at least a portion thereof, and a curved inner surface, a portion of the length of the at least an outer electrode segment overlapping a portion of the length of the at least an inner electrode segment and forming an analyzer region therebetween, the at least an outer electrode segment being approximately coaxially aligned with the at least an inner electrode segment, at least one of the inner and outer electrode assemblies comprising a segmented electrode assembly having at least first and second and third segmented electrode segments and a length, disposed adjacent another electrode having a length, the second segmented electrode segment disposed intermediate the first and third segmented electrode segments in an end-to-end arrangement, a surface of the segmented electrode disposed opposite to a surface of the other electrode; and, at least a first contact on at least one of the other electrode and the second segmented electrode segment for receiving a first direct current voltage between the other electrode and the second segmented electrode segment, and for applying an asymmetric waveform to at least one of the other electrode and the second segmented electrode segment, whereby during use the second segmented electrode segment is maintained at a different potential relative to the first and third segmented electrode segments, such that a potential gradient is formed in a direction along the length of the segmented electrode assembly.

In accordance with the invention there is provided another apparatus for separating ions, comprising: an analyzer region defined by a space between first and second electrodes, the first electrode having a length and at least a quadratic ruled outer surface, the second electrode overlapping the first electrode along a first portion of the length thereof and having at least a quadratic ruled inner surface opposite to the at least a quadratic ruled outer surface of the first electrode; at least a first contact on at least one of the first and second electrodes for receiving a first direct current voltage, and for applying an asymmetric waveform voltage to the at least one of the first and second electrodes; a third electrode aligned with the second electrode for defining a space between the third electrode and the first electrode, the third electrode overlapping the first electrode along a second portion of the length thereof adjacent to the first portion of the length thereof and other than overlapping with the first portion of the length thereof; and, a second contact on the third electrode for at least one of receiving a second direct current voltage and applying the asymmetric waveform voltage to the third electrode, whereby during use the third electrode is maintained at a different potential relative to the second electrode, such that a potential gradient is formed in a direction along the length of the first electrode.

In accordance with the invention there is provided yet another apparatus for separating ions, comprising: an inner electrode having a length and an outer surface that is curved in a direction transverse to its length and an outer electrode having a length, a channel through a portion thereof, and a curved inner surface, a portion of the length of the outer electrode overlapping a portion of the length of the inner electrode and forming an analyzer region therebetween, the outer electrode being approximately coaxially aligned with the inner electrode, the outer electrode including an ion inlet orifice and an ion outlet orifice defined one each within facing surface portions within the length of the outer electrode overlapping a portion of the length of the inner electrode, at least one of the inner and outer electrodes comprising a segmented electrode comprised of an electrode segment assembly, the electrode segment assembly including a plurality of electrode segments extending approximately a length coinciding with the length of the at least one of the inner and outer electrode, a surface of each of the electrode segments being opposite a surface of the other one of the inner and outer electrode; at least a first contact on one of the other one of the inner and outer electrode and a first segment of the segmented electrode for receiving a first direct current voltage, and for applying an asymmetric waveform to the one of the other one of the inner and outer electrode and the first segment of the segmented electrode; and, at least a second contact on a second segment of the segmented electrode for receiving a second direct current voltage, so as to form a potential gradient in a direction along the lengths of the inner and outer electrodes.

In accordance with another aspect of the invention there is provided a method for separating ions, comprising the steps of: providing an analyzer region defined by a space between first and second spaced apart electrodes; introducing ions into the analyzer region; providing a flow of a carrier gas through the analyzer region for directing the ions along a first direction within the analyzer region; providing a first electric field component within the analyzer region resulting from the application of an asymmetric waveform voltage and a direct current compensation voltage to at least one of the first and second electrodes, for directing the ions along a second direction within the analyzer region that is approximately perpendicular to the first direction; and, providing a second electric field component within the analyzer region for directing the ions along a third direction within the analyzer region, the third direction being approximately perpendicular to each one of the first direction and the second direction.

In accordance with the other aspect of the invention there is provided a method for separating ions, comprising the steps of: providing an analyzer region defined by a space between inner and outer electrodes having at least a quadratic ruled surface, the inner electrode having a length, the outer electrode overlapping the inner electrode along a potion of the length thereof, transporting ions along an average ion flow path within the analyzer region, the average ion flow path extending in a first direction approximately transverse to the length of the inner electrode and absent a substantially linear portion, the average ion flow path extending between an ion inlet orifice of the analyzer region and an ion outlet orifice of the analyzer region; providing a radial electric field component within the analyzer region resulting from the application of an asymmetric waveform voltage and a direct current compensation voltage to at least one of the inner and outer electrodes for effecting a separation of the ions; and, providing a longitudinal electric field component within the analyzer region for directing ions within the analyzer region in a second direction along the length of the inner electrode, the second direction being approximately perpendicular to the first direction.

In accordance with the invention there is provided yet another apparatus for separating ions, comprising: an inner electrode and an outer electrode arranged in an overlapping coaxial arrangement so as to form an analyzer region therebetween; at least a first contact on at least one of the inner electrode and the outer electrode for providing a first direct current voltage difference between the inner electrode and the outer electrode, and for applying an asymmetric waveform to at least one of the inner electrode and the outer electrode; an ion inlet orifice within a first surface portion of the outer electrode for introducing ions into the analyzer region and an ion outlet orifice within a second surface portion of the outer electrode for extracting ions from the analyzer region, the first surface portion approximately facing the second surface portion; wherein at least one of the inner electrode and the outer electrode comprises a segmented electrode comprising a first electrode segment having at least a second contact for providing a second direct current voltage potential difference between the first electrode segment and the other one of the inner electrode and the outer electrode.

BRIEF DESCRIPTION OF THE DRAWINGS

Exemplary embodiments of the invention will now be described in conjunction with the following drawings, in which similar reference numbers designate similar items:

FIG. 1b is a side elevational view of the cylindrical side-to-side FAIMS device shown in FIG. 1a;

FIG. 4 is a simplified side view of a segmented side-to-side FAIMS device;

FIG. 5 is an enlarged side view of a portion of the segmented side-to-side FAIMS device of FIG. 4;

FIG. 6 is a top view of the segmented side-to-side FAIMS device of FIG. 4;

DETAILED DESCRIPTION OF THE INVENTION

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein.

Figure 1A:
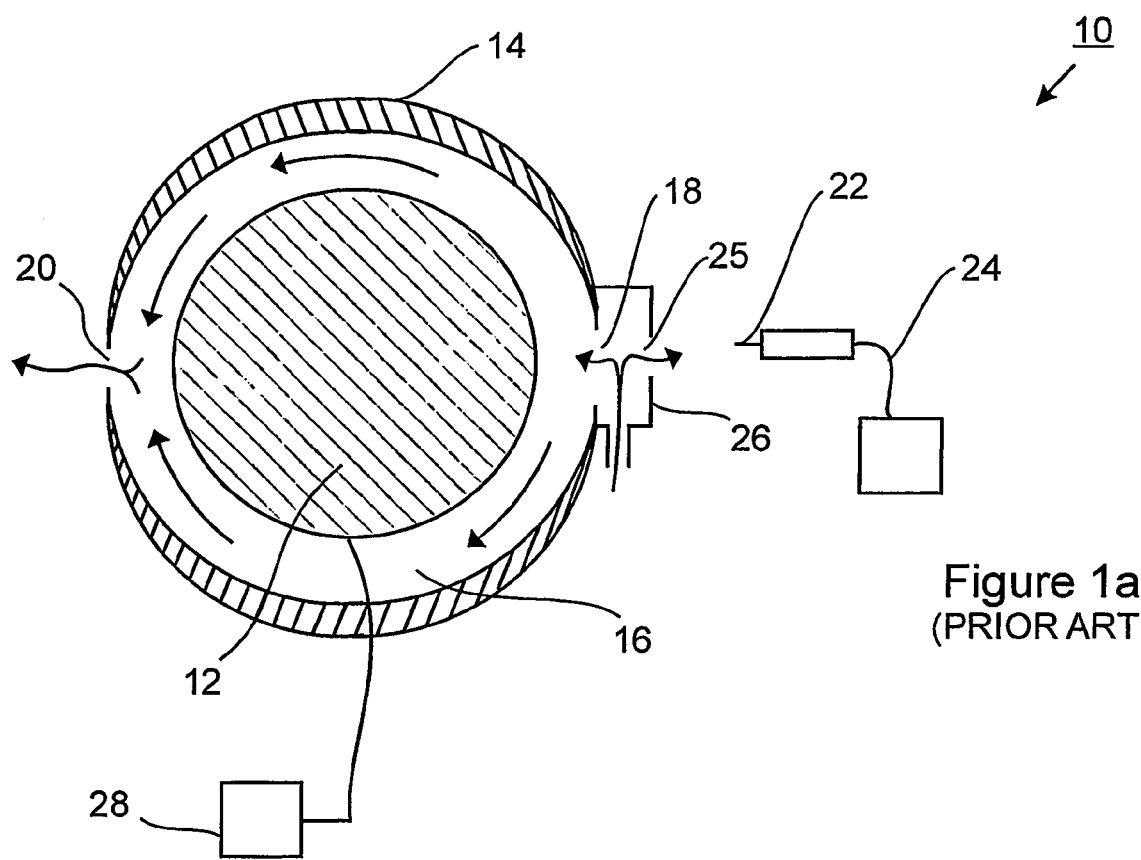
FIG. 1a is a simplified cross sectional view of a cylindrical side-to-side FAIMS device according to the prior art.

Referring to FIG. 1a, shown is a simplified cross sectional view of a cylindrical side-to-side FAIMS according to the prior art. The cylindrical side-to-side FAIMS device, shown generally at 10, includes inner and outer cylindrical electrodes 12 and 14, respectively, which are supported by an electrically insulating material (not shown) in an overlapping, spaced-apart arrangement. The generally annular space between the inner electrode 12 and the outer electrode 14 defines a FAIMS analyzer region 16. The analyzer region 16 is of approximately uniform width and extends around the circumference of the inner electrode 12. An ion inlet orifice 18 is provided through the outer electrode 14 for introducing ions from an ion source into the analyzer region 16. For example, the ion source is in the form of an electrospray ionization ion source including a liquid delivery capillary 24, a fine-tipped electrospray needle 22 that is held at high voltage (power supply not shown), and a curtain plate 26 serving as a counter-electrode for the electrospray needle 22. Of course, any other suitable ionization source is optionally used in place of the electrospray ionization ion source. A flow of a carrier gas, which is represented in the figure by a series of closed-headed arrows, is provided within the analyzer region 16 to carry the ions around the inner electrode 12 and toward an ion outlet orifice 20. An orifice 25 within the curtain plate electrode 26 allows for the flow of a portion of the carrier gas in a direction that is counter-current to the direction in which the ions are traveling near the ion inlet orifice 18, so as to desolvate the ions before they are introduced into the analyzer region 16. The inner electrode 12 is in electrical communication with a power supply 28 that during use is capable of applying a high voltage asymmetric waveform voltage (DV) and a low voltage dc compensation voltage (CV) to the inner FAIMS electrode 12.

Still referring to FIG. 1a, ions are produced in the gas phase at the fine-tipped electrospray needle 22 from a suitable sample containing a species of interest. Typically, a mixture including a plurality of different ion types is produced when the sample is ionized. The potential gradient accelerates the ions of the mixture away from the electrospray needle 22, toward the curtain plate electrode 26. A portion of the ions pass through the orifice 25 in the curtain plate electrode 26, become entrained in the carrier gas flow and are carried into the FAIMS analyzer region 16. Once inside the FAIMS analyzer region 16, the ions are carried through an electric field that is formed within the FAIMS analyzer region 16 by the application of the DV and the CV to the inner FAIMS electrode 12. Ion separation occurs within the FAIMS analyzer region 16 on the basis of the high field mobility properties of the ions. Those ions of the mixture that have a stable trajectory for a particular combination of DV and CV are selectively transmitted through the FAIMS analyzer region 16, whilst other ions of the mixture collide with an electrode surface and are lost. The selectively transmitted ions are extracted from the analyzer region 16 via ion outlet orifice 20 and are typically subjected to one of detection and further analysis.

Figure 1B:
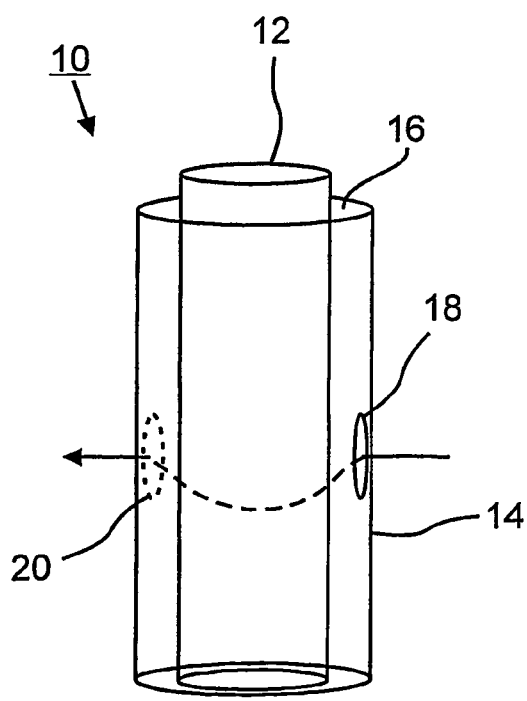

Referring now to FIG. 1b, shown is a simplified side elevational view of the cylindrical side-to-side FAIMS of FIG. 1a. Elements labeled with the same numerals have the same function as those illustrated in FIG. 1a. The dotted line extending between ion inlet orifice 18 and ion outlet orifice 20 represents one possible average ion flow path around the inner electrode 12. An average ion flow path is defined as the net trajectory of an ion as a result of a carrier gas flow through the analyzer region, although the individual ion also experiences an oscillatory motion between the electrodes as a result of the applied asymmetric waveform voltage. In particular, the dotted line represents one of two shortest average ion flow paths through the analyzer region 16, one shortest average ion flow path extending in each direction around the inner electrode 12. Of course, when many like-charged ions are present within the analyzer region, ion-ion repulsion forces tend to cause the ions to spread out slightly along the length of the inner electrode 12. Accordingly, some selectively transmitted ions migrate into portions of the analyzer region where the gas flow rate is low or stagnant, making their extraction from the analyzer region difficult.

Figure 2:
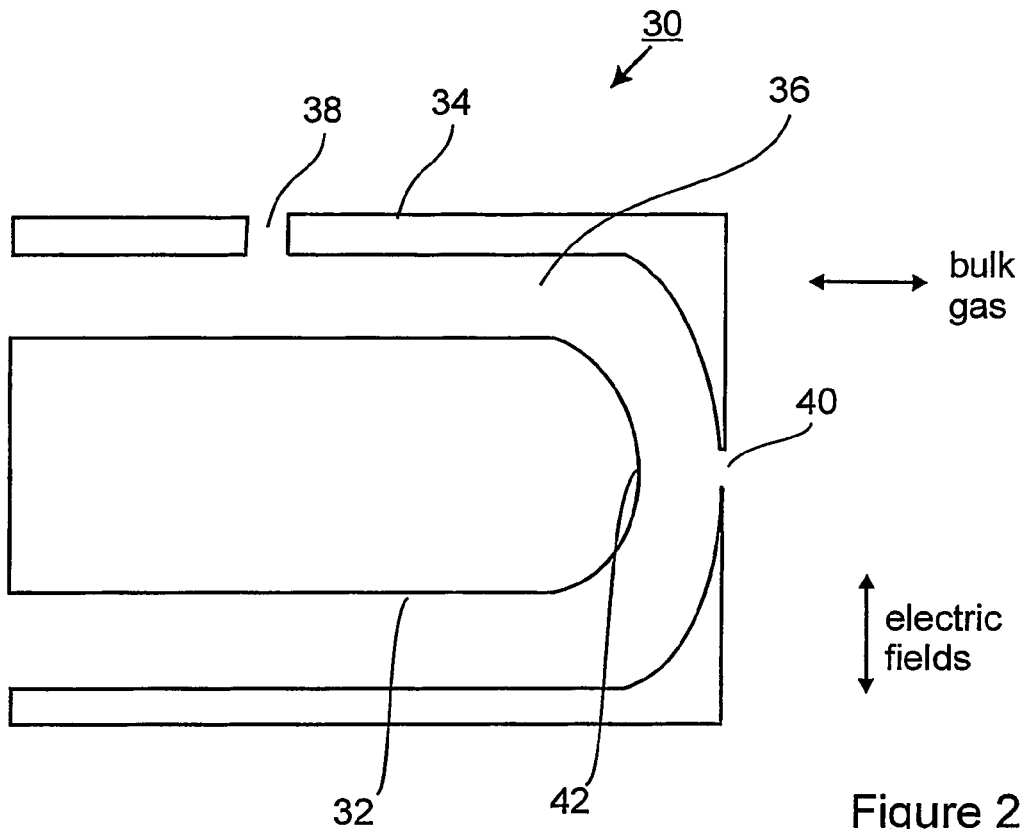
FIG. 2 is a side cross-sectional view of a domed-FAIMS device.

Referring now to FIG. 2, shown is a side cross-sectional view of a domed-FAIMS device. The domed-FAIMS, shown generally at 30, includes inner and outer cylindrical electrodes 32 and 34, respectively, in a spaced apart arrangement defining an analyzer region 36 therebetween for separating ions introduced via an ion inlet orifice 38. In particular, FIG. 2 illustrates the manner in which the electric fields and the gas flows interact with the ions within the analyzer region 36. The electric fields restrict the movement of the ions between the electrodes, in a radial direction defined with respect to the center of the inner electrode 32 being taken as the axis of rotation, whereas the carrier gas flows along the length of the analyzer region 36 to transport the ions from an ion inlet orifice 38 toward an ion outlet orifice 40. At the region in front of a hemispherical tip 42 of the inner electrode, the ions are directed toward the ion outlet orifice 40 as a narrow beam that is suitable for introduction into a not illustrated mass spectrometer.

Figure 3:
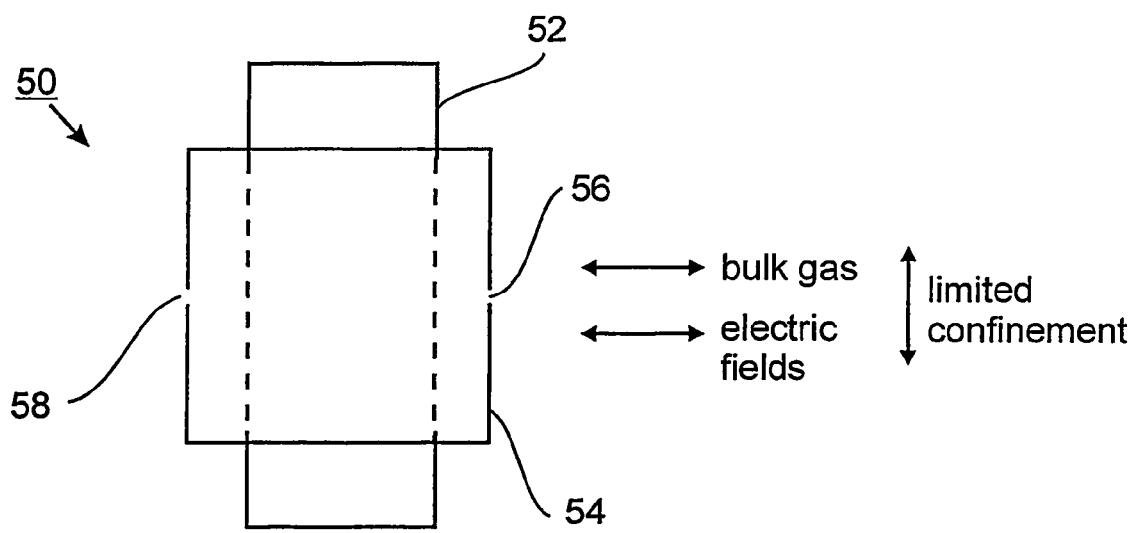
FIG. 3 is a simplified side view of a cylindrical side-to-side FAIMS device.

Referring now to FIG. 3, shown is a simplified side view of a cylindrical side-to-side FAIMS device. With the side-to-side version of FAIMS, shown generally at 50, the electric fields again work to keep the ions between an inner and an outer electrode 52 and 54, respectively. The electric fields restrict the movement of the ions between the electrodes, in a radial direction defined with respect to the center of the inner electrode 52 being taken as the axis of rotation; however, the carrier gas fans out between an ion inlet orifice 56 and an ion outlet orifice 58, so as to transmit ions along a plurality of average ion flow paths therebetween. Only a portion of the ions introduced through the ion inlet orifice 56 follow a shortest ion average flow path to the ion outlet orifice 58. Accordingly, ion losses due to diffusion and space charge repulsion are increased in a side-to-side FAIMS device 50 relative to a dome FAIMS device 30. Of course, ion losses due to diffusion and space charge repulsion are expected to be the most pronounced for ions with higher mobility values, such as for instance chloride ions, and least noticeable for ions with lower mobility values, such as for instance protein ions.

Referring now to FIG. 4, shown is a simplified side view of a segmented side-to-side FAIMS device according to the instant invention. FIG. 4 shows only the conductive components of this device; for instance, the insulating PEEK material and some of the components of ionization source have been omitted for the sake of clarity. The segmented side-to-side FAIMS, shown generally at 60, includes a cylindrical inner electrode 62 as well as first, second and third outer electrode segments 64, 66 and 68, respectively, which are supported by not illustrated electrically insulating material in an overlapping, spaced-apart arrangement with the inner electrode 62. The generally annular space between the inner electrode 62 and the second outer electrode segment 66 defines a FAIMS analyzer region 70. The analyzer region 70 is of approximately uniform width and extends around the circumference of the inner electrode 62 between an ion inlet orifice 72 and an ion outlet orifice 74. The ion inlet orifice 72 is provided through the second outer electrode segment 66 for introducing ions from an ion source into the analyzer region 70. For example, the ion source is in the form of an electrospray ionization ion source including a liquid delivery capillary 76, a fine-tipped electrospray needle 78 that is held at high voltage (power supply not shown), and a curtain plate 80 serving as a counter-electrode for the electrospray needle 78. Of course, any other suitable ionization source is used optionally in place of the electrospray ionization ion source. A flow of a carrier gas, which is represented in the figure by a series of closed-headed arrows, is provided within the analyzer region 70 to carry the ions around the inner electrode 62 and toward the ion outlet orifice 74. An orifice 81 within the curtain plate electrode 80 allows for the flow of a portion of the carrier gas in a direction that is counter-current to the direction in which the ions are traveling near the ion inlet orifice 72, so as to desolvate the ions before they are introduced into the analyzer region 70. The inner electrode 62 is in electrical communication with a power supply 82 that during use is capable of applying a high voltage asymmetric waveform voltage (DV) and a low voltage dc compensation voltage (CV) to the inner FAIMS electrode 62.

Referring still to FIG. 4, the inner electrode 62 remains unchanged from prior art side-to-side FAIMS devices, whilst the outer FAIMS electrode is provided as an assembly of three separate outer electrode segments 64, 66 and 68, all of which are electrically isolated one from another. A power supply 90 is provided in electrical communication with the first outer electrode segment 64 that during use is capable of applying a dc offset potential to the first outer electrode segment 64. For instance, the power supply 90 applies a dc potential in the range of 0–50 volts relative to the second outer electrode segment 66. Most preferably, the power supply 90 applies a dc potential in the range of 0–15 volts relative to the second outer electrode segment 66. Of course, the polarity of the voltage may be either positive or negative, and is determined in dependence upon the polarity of the ions being selectively transmitted within the analyzer region 70. A power supply 88 is also shown in electrical communication with the third outer electrode segment 68 for applying a dc offset potential to the third outer electrode segment 68. Optionally, a single power supply in electrical communication with the first and third outer electrode segments replaces the two separate power supplies 88 and 90. Of course, when a single power supply is used, it is not possible to apply different dc offset potentials individually to the first and third outer electrode segments.

Of course, a separate power supply (not shown) is also provided in electrical communication with the second outer electrode segment 66 for maintaining the second outer electrode segment 66 at a desired dc voltage.

Referring still to FIG. 4, the segmented side-to-side FAIMS device 60 is sealed gas tight against an orifice plate 84 of a not illustrated mass spectrometer. Additionally, the FAIMS device 60 is assembled such that there is no gas leaks, in other words, the carrier gas and ions are only able to enter or exit the space between the inner electrode 62 and the outer electrode segments 64, 66 and 68 through one of the ion inlet orifice 72 and the ion outlet orifice 74, respectively, both of which are located in the second outer electrode segment 66. To this end, an insulating material (not shown) is disposed between opposing ends of outer electrode segments 64 and 66, and between opposing ends of outer electrode segments 66 and 68. The insulating material is selected to maintain electrical isolation of the various conductive surfaces shown in FIG. 4. PEEK is one suitable material for use as the insulating material.

Referring now to FIG. 5, shown is an enlarged side view of a portion of the segmented side-to-side FAIMS device 60 shown at FIG. 4. In particular, FIG. 5 shows an enlarged view of the region in which the orifice plate 84, the first outer electrode segment 64, and the second outer electrode segment 66 are combined. Insulating material 86 is shown in the enlarged view, and is represented by the dotted lines between the various conductive surfaces. The insulating material 86 preferably satisfies a number of criteria. First, the insulating material 86 maintains electrical isolation of the various conductive surfaces shown in FIG. 4, such as for example between adjacent outer electrode segments. Preferably, the insulating material 86 is thin, such that the electric fields in the analyzer region are not adversely affected by a charge build-up on the insulating material 86, in particular between the outer electrode segments. Additionally, the insulating material 86 that is disposed between the first outer electrode segment 64 and the second outer electrode segment 66, and between the second outer electrode segment 66 and the third outer electrode segment 68, should not extend inside of the inner wall of any of the outer electrode segments. Most preferably, the insulating material is recessed within the space that is formed between adjacent outer electrode segments. Of course, the insulating material 86 preferably forms a gas-tight seal between the conductive surfaces so as to prevent gas from escaping between the conductive surfaces, which would lead to additional ion losses. For example, carrier gas escaping through other than the ion outlet orifice 74 reduces the total flow through the analyzer region 70 and into the not illustrated mass spectrometer, which results in increased ion transit time through the device 60 and increased ion losses, respectively. Furthermore, a flow of carrier gas escaping from between the electrodes may carry ions toward the electrodes, leading to a higher number of ions being lost as a result of a collision with an electrode surface, thereby further decreasing ion transmission efficiency. Alternatively, the insulating material 86 does not form a gas-tight seal between the conductive surfaces, and the effects of the gas escaping from between the conductive surfaces are compensated for. For instance, a supplemental flow of carrier gas is introduced into the analyzer region 70 through the spaces between the conductive surfaces, so as to reduce ion loss.

Referring now to FIG. 6, shown is a top view of the segmented side-to-side FAIMS device shown at FIG. 4. FIG. 6 shows an example of one preferred configuration of the insulating material 86. In particular, the insulating material between adjacent outer electrode segments is provided in the form of a ring of insulating material that is thin both in the radial and longitudinal directions. As shown in FIG. 6, the ring of insulating material is thin compared to the wall thickness of the outer electrode segments. Of course, any suitable material may be used as the insulating material 86, such as for example one of PEEK and Teflon™ tape. Preferably, Teflon™ tape is used in applications where the voltage difference is small, such as for example less than 10V. In particular, Teflon™ tape may be used between the orifice plate 84 and each one of the outer electrode segments.

During use, ions are produced in the gas phase for introduction into the segmented side-to-side FAIMS device 60 from a suitable sample containing a species of interest. Typically, a mixture including a plurality of different ion types is produced when the sample is ionized. The potential gradient accelerates the ions of the mixture away from the electrospray needle 78, toward the curtain plate electrode 80. A portion of the ions pass through the orifice 81 in the curtain plate electrode 80, become entrained in the carrier gas flow and are carried into the FAIMS analyzer region 70. Once inside the FAIMS analyzer region 70, the ions are carried through an electric field that is formed within the FAIMS analyzer region 70 by the application of the DV and the CV to the inner FAIMS electrode 62. Ion separation occurs within the FAIMS analyzer region 70 on the basis of the high field mobility properties of the ions. Those ions of the mixture that have a stable trajectory for a particular combination of DV and CV are selectively transmitted through the FAIMS analyzer region 70, whilst other ions of the mixture collide with an electrode surface and are lost. The selectively transmitted ions are extracted from the analyzer region 70 via ion outlet orifice 74 and are typically subjected to one of detection and further analysis.

The ions with the appropriate properties for transmission for a given set of applied experimental conditions are confined in a radial direction between the second outer electrode segment 66 and the inner electrode 62. When all of the outer electrode segments 64, 66, 68 are at the same applied dc voltage, however, diffusion and space charge repulsion act to displace ions away from regions of higher ion density, such as for example along an axis intersecting the ion inlet orifice 72 and ion outlet 74. Referring again to FIG. 4, an ion that is located at position A is within the region of higher ion density, an ion that is located at position B is within a region of intermediate ion density, and an ion that is located at position C is within a region of relatively low ion density. For the purposes of the following discussion, each one of the ions that are located at positions A, B and C are assumed to be positive ions with identical ion mobility properties.

By placing a positive dc voltage on the first outer electrode segment 64 and the third outer electrode segment 68 relative to the second outer electrode segment 66, for example, +5 V, an electric field is established along the length of the electrodes of the segmented side-to-side device 60. This electric field acts to minimize losses due to diffusion and space charge repulsion, and therefore increases ion transmission efficiency. The effect of the electric fields in the longitudinal direction on the ion that is located at position B is to push the ion back toward location A. Of course, in addition to being pushed back toward location A the ion also experiences a push toward the inner electrode.

In the case of an ion that is located at position C, changing the dc voltage on the first outer electrode segment 64, relative to the second outer electrode segment 66, causes the CV between the first outer electrode segment 64 and the inner electrode 62 to be different than the CV between the second outer electrode segment 66 and the inner electrode 62. Consequently, instead of having the desired effect of pushing the ion back toward location A to prevent ion loss, the application of the dc voltage causes the ion that was focused between the first outer electrode segment 64 and the inner electrode 62, when no dc voltage was applied, to collide with the inner electrode. Accordingly, the voltages that are applied to the first and third outer electrode segments 64, 68, respectively, must be optimized so that any fringing fields resulting from these voltages do not significantly disrupt the focusing fields that are required for efficient ion transmission within the analyzer region 70 between the second outer electrode segment 66 and the inner electrode 62.

Referring again to FIG. 4, each one of the outer electrode segments is shown as being substantially the same size, in terms of the length axis. Optionally, the individual outer electrode segments are of different lengths. For instance, the first outer electrode segment 64 and the third outer electrode segment 68 are of a same length that is longer than the length of the second outer electrode segment 66. The length of each individual outer electrode segment, as well as the dc offset voltages applied to the first outer electrode segment 64 and to the third outer electrode segment 68, can be optimized experimentally. Optionally, segment lengths and dc offset voltages are predetermined for particular applications. Further optionally, a number of outer electrode segments other than three is used.

The concepts applied in the construction of a segmented side-to-side FAIMS device have been illustrated for one particular embodiment of a segmented side-to-side FAIMS device, namely a side-to-side FAIMS device comprising a cylindrical inner electrode and a threefold-segmented outer electrode. A person of skill in the art realises that the ideas illustrated above are to be generalized to include various shapes of inner and outer electrodes, as well as various types of electrode segmentation patterns.

Generally, the shape of the inner and outer electrodes is chosen such that the surfaces of the inner and outer electrodes, which constitute the boundaries of an analyzer region, include but are not limited to quadratic ruled surfaces and surfaces of revolution. Examples for quadratic ruled surfaces are the cylinder, the elliptic cylinder, the hyperboloid, and the elliptic hyperboloid. Alternatively, the surfaces of the inner and outer electrodes enclosing the analyzer region are expressed as superposition of quadratic ruled surfaces. Further alternatively, the surfaces have a crosssection in a plane parallel to the average ion flow path that is curved in perimeter. Preferably the perimeter has equal distances along each of two paths between the ion inlet orifice and the ion outlet orifice. Alternatively, the perimeter includes at least one curved line symmetric about a line formed between the ion inlet orifice and the ion outlet orifice. Preferably, at most two curved lines form the perimeter. Further preferably, a curved surface of an electrode is curved in a direction transverse to a length of the electrode.

The surface of the inner electrode forming a boundary of an analyzer region is also referred to as the outer surface of the inner electrode, and the surface of the outer electrode forming a boundary of an analyzer region is also referred to as the inner surface of the outer electrode. The outer surface of the inner electrode as well as the inner surface of the outer electrode are adjacent to each other, and opposing points on the inner and outer surface are all spaced apart by approximately a constant distance, or by variable distances.

Figure 7A:
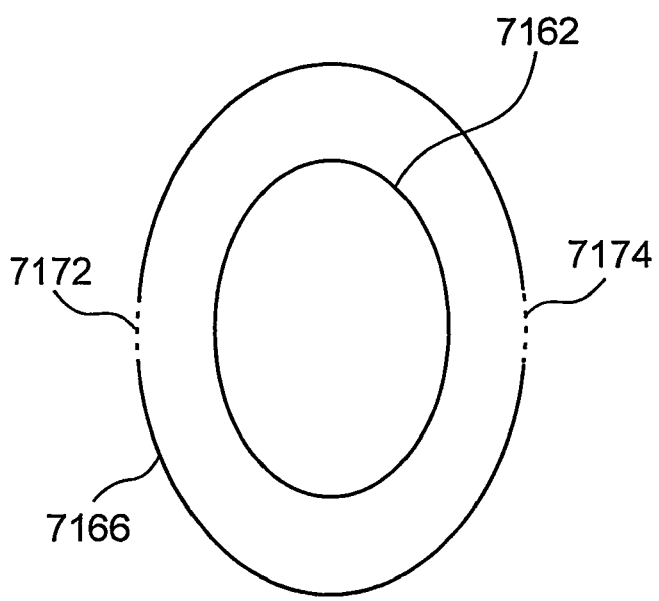
FIG. 7a is a top view of a side-to-side FAIMS device, in which an inner electrode has elliptic cylindrical shape.
Figure 7B:
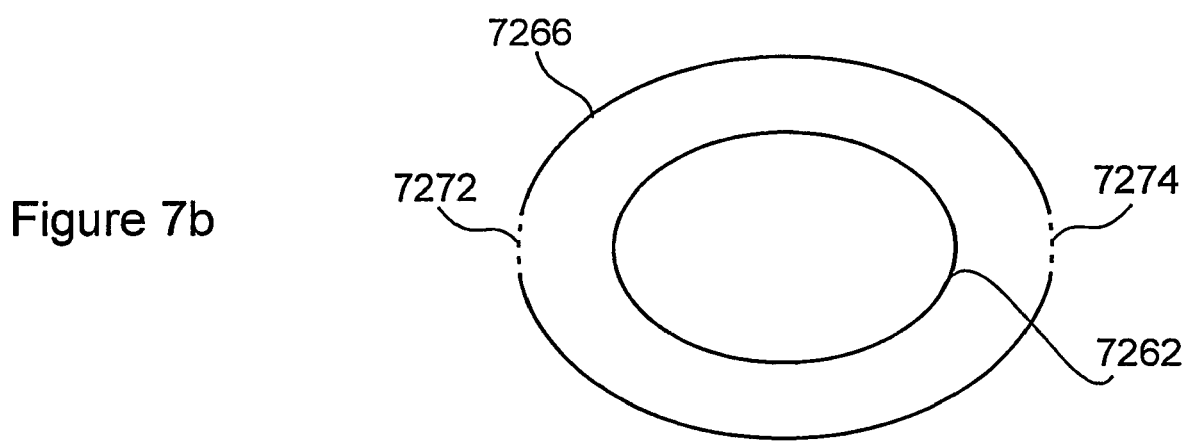
FIG. 7b is a top view of another side-to-side FAIMS device, in which an inner electrode has an elliptic cylindrical shape.
Figure 7C:
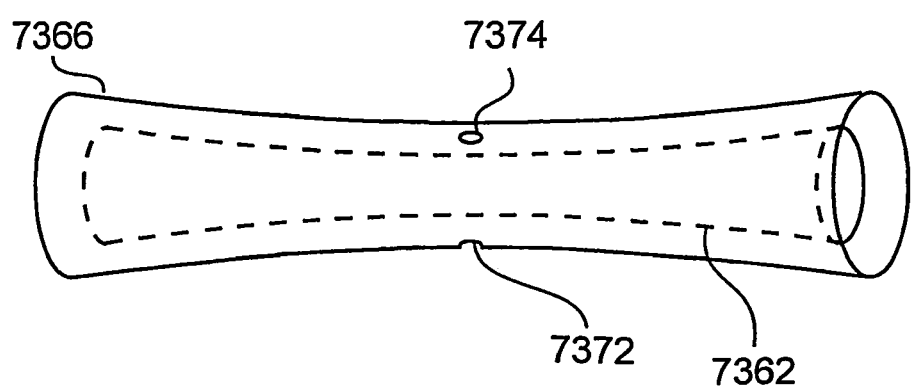
FIG. 7c is a top view of a side-to-side FAIMS device, in which an inner electrode has an elliptic hyperbolical shape.

In FIGS. 7a–c, shown are top views of three different electrode configurations of a segmented side-to-side FAIMS device according to embodiments of the instant invention. Referring to FIG. 7a, an inner electrode 7162 has an elliptic cylindrical shape, and is oriented relative to an outer electrode 7166 such that the major axis of the elliptical cross section is substantially perpendicular to the line connecting an ion inlet orifice 7172 and an ion outlet orifice 7174, both disposed in the outer electrode 7166. The outer electrode 7166 has an inner surface of elliptic cylindrical shape, so as to maintain an approximately uniform spacing between the electrode segments enclosing the analyzer region.

Referring now to FIG. 7b, an inner electrode 7262 has an elliptic cylindrical shape, and is oriented relative to an outer electrode 7266 such that the major axis of the elliptical cross section is substantially parallel to the line connecting an ion inlet orifice 7272 and an ion outlet orifice 7274, both disposed in the outer electrode 7266. The outer electrode 7266 has an inner surface that is of elliptic cylindrical shape, so as to maintain an approximately uniform spacing between the electrode segments enclosing the analyzer region.

Referring to FIG. 7c, an inner electrode 7362 has an elliptic hyperbolical shape, and is oriented relative to an outer electrode 7366 such that line connecting the two foci of an hyperbolic cross section is substantially perpendicular to the line connecting an ion inlet orifice 7372 and an ion outlet orifice 7374, both disposed in the outer electrode 7366. The outer electrode 7366 has an inner surface that is of elliptic hyperbolical shape, so as to maintain an approximately uniform spacing between the electrode segments enclosing the analyzer region.

Alternatively, an inner electrode and an outer electrode have different shapes. The outer surface of an inner electrode for example has an elliptic cylindrical shape, whereas the inner surface of an outer electrode has a regular cylindrical shape. The varying distance between inner and outer electrode is possibly favourably utilized for analyzing an ion beam containing a plurality of distinct ions. A person of skill in the art easily envisions different electrode configurations, for all of which the surfaces enclosing an analyzer region are describable as superposition of quadratic ruled surfaces.

Figure 8A:
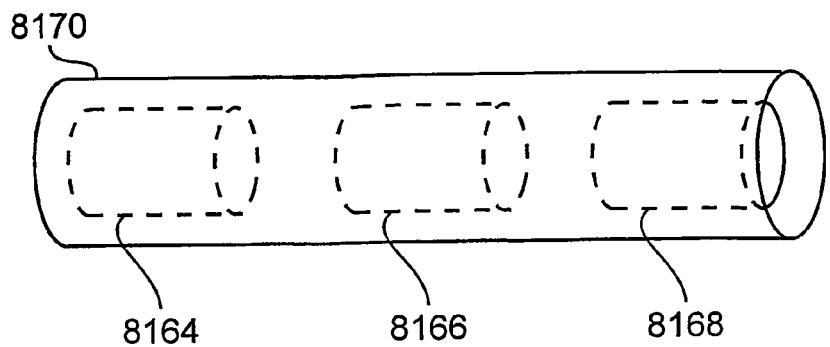
FIG. 8a, is a longitudinal cross sectional view through a side-to-side FAIMS device having a segmented inner electrode.

In the examples given above, electrode segmentation has been described for cases in which an outer electrode is segmented into three separate outer electrode segments. An intermediate segment of the outer electrode, and the inner electrode constitute an analyzer region of a side-to-side FAIMS device, whereas outer segments of the outer electrode focus an ion beam, and provide functionality of an ion lens. Alternatively, this functionality is also achieved when the inner electrode is segmented. Referring now to FIG. 8a, shown is a longitudinal cross sectional view through a segmented side-to-side FAIMS device. Three inner electrode segments 8164, 8166 and 8168 are provided, as well as an outer electrode 8170. The inner electrode segment 8166 and the corresponding part of the outer electrode 8170 constitute the analyzer region of the FAIMS device, whereas the inner electrode segments 8164 and 8168 provide similar functionality as described for the electrode segments 64 and 68 (i.e. during use a high voltage asymmetric waveform voltage and a low voltage dc compensation voltage is applied between the inner electrode segment 8166 and the outer electrode 8170. and a high voltage asymmetric waveform voltage and a low voltage dc compensation voltage is applied between each inner electrode segment 8164 or 8168 and the outer electrode 8170).

Figure 8B:
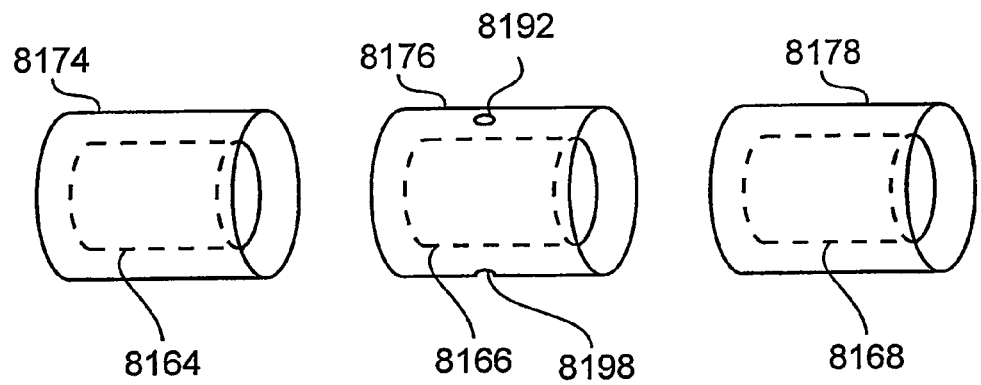
FIG. 8b, is a longitudinal cross sectional view through a side-to-side FAIMS device having a segmented inner electrode, and a segmented outer electrode.

Referring now to FIG. 8b, shown is a longitudinal cross sectional view through a side-to-side FAIMS device, having segmented inner as well as outer electrodes. The inner electrode is segmented into a first inner electrode segment 8164, a second inner electrode segment 8166, and a third inner electrode segment 8168. The outer electrode is segmented into a first outer electrode segment 8174, a second outer electrode segment 8176, and a third outer electrode segment 8178. The inner electrode segment 8166 and the outer electrode segment 8176 constitute the analyzer region of the side-to-side FAIMS device, whereas the remaining electrodes function as to enhance, guide, and focus an ion beam. An ion inlet orifice 8192 and an ion outlet orifice 8198 are both disposed in the outer electrode segment 8176. In the discussion that follows, the first inner electrode segment 8164 and the first outer electrode segment 8174 comprise a first electrode segment pair. Second and third electrode segment pairs are similarly defined in terms of the remaining inner and outer electrode segments.

When both the inner electrode and the outer electrode are segmented, it is preferable to separately apply a same DV between each inner/outer electrode segment pair. The potentials that are applied to the inner and outer electrode segments of each one of the first and third inner/outer electrode segment pairs are floated relative to the potentials that are applied to the second inner/outer electrode pair, while maintaining a same CV value between each of the first, second, and third inner/outer electrode segment pairs. Accordingly, a same combination of CV and DV exists for selectively transmitting an ion of interest between each inner/outer electrode segment pair. Since the dc potentials applied to each one of the first and third electrode segment pairs are "floated" relative to the second electrode segment pair, ions being transmitted between the second inner/outer electrode segment pair from the ion inlet orifice to the ion outlet orifice will "see" a potential gradient near an interface between the second inner/outer electrode segment pair and each one of the first and third inner/outer electrode segment pairs. This potential gradient tends to prevent the ions from spreading out into a space between either one of the first and third inner/outer electrode segment pairs, even though appropriate conditions for transmitting the ions exist within the space.

Figure 8C:
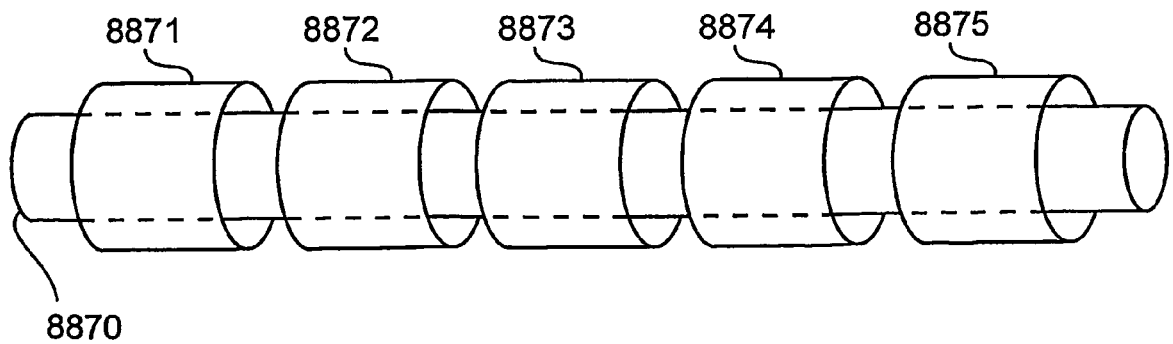
FIG. 8c is a longitudinal cross sectional view through a side-to-side FAIMS device having a segmented outer electrode including five sections, and, FIG. 9 is a simplified flow diagram for a method of longitudinally confining ions within a side-to-side FAIMS device.

Referring to FIG. 8c, another embodiment of the invention is shown wherein an outer electrode is segmented circumferentially into five peripheral sections 8871, 8872, 8873, 8874, and 8875, the peripheral sections enclosing an inner electrode 8870. Sections 8872 and 8874 serve as analyzer sections, whereas sections 8871, 8873, and 8875 serve as boundary sections. It is of advantage that section 8873 serves as boundary section not only for one, but for two analyzer sections. Of course, other numbers of electrodes are also supported. The sections allow for application of different bias voltages at different locations within the peripheral sections. Of course, other applications of the segmented electrodes are also supported. Optionally, it is the inner electrode that is segmented in a similar fashion.

Of course, the segmentation of the FAIMS analyser in accordance with the invention is also useful for providing non-overlapping analyser regions that are isolated one from another.

Figure 9:
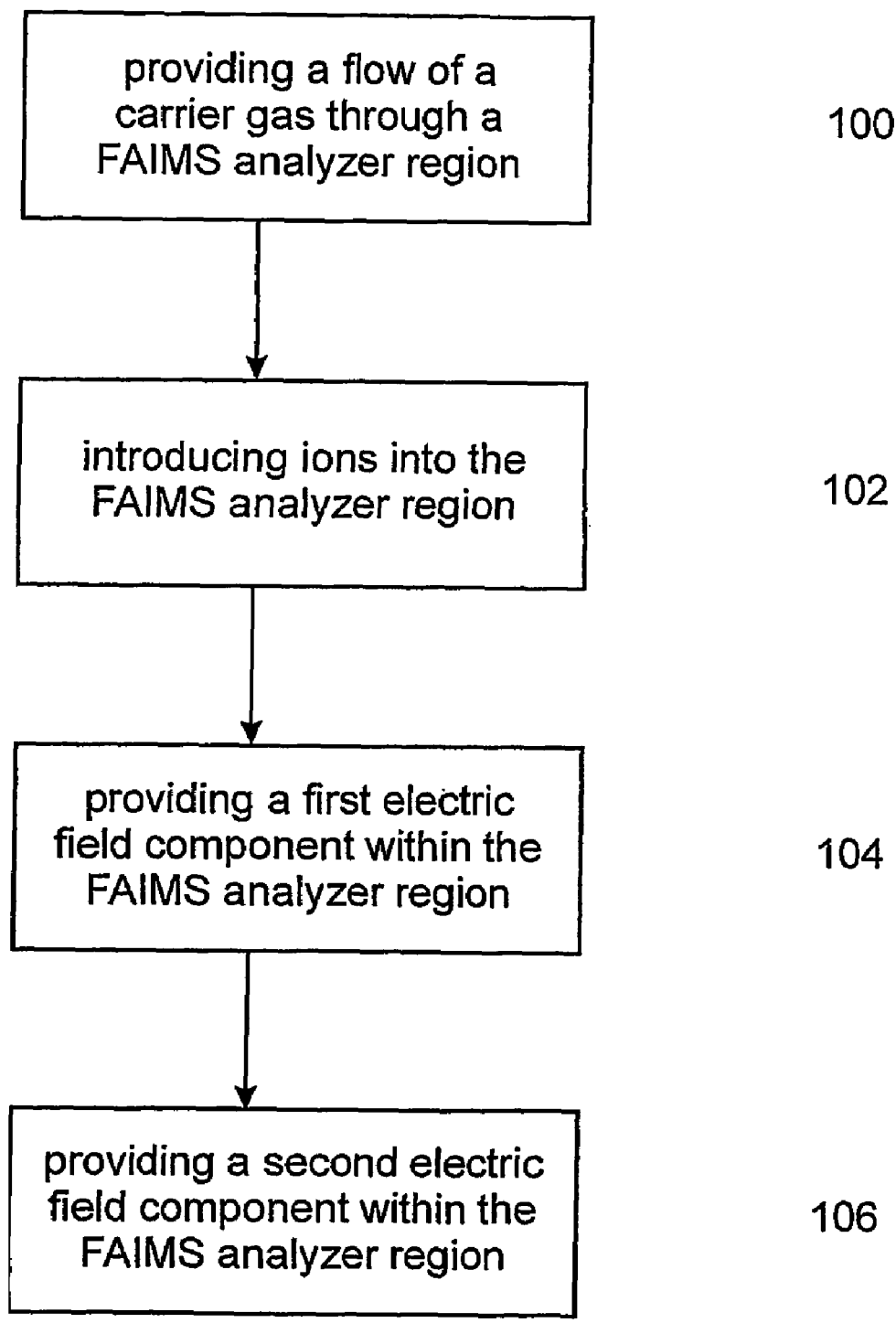

Referring now to FIG. 9, shown is a simplified flow diagram for a method of improving ion transmission efficiency of a side-to-side FAIMS device by longitudinally confining the ions during separation. At step 100, a flow of a carrier gas is provided through an analyzer region of a segmented side-to-side FAIMS device, such as device 60 shown at FIG. 4. At step 102 ions are introduced into the analyzer region, for instance the ions are produced at an ion source, entrained into the flow of the carrier gas and subsequently carried into the analyzer region with the carrier gas. At step 104, a first electric field component is provided within the analyzer region, the first electric field component resulting from the application of an asymmetric waveform voltage and a direct current compensation voltage to at least one of the inner electrode 62 and the first, second, and third outer electrode segments 64, 66 and 68, respectively. The first electric field component is a radial electric field component for focusing the selectively transmitted ions as they move through the analyzer region. At step 106, a second electric field component is provided within the analyzer region. For instance, a positive dc potential is applied to each one of the first outer electrode segment 64 and the third outer electrode segment 68, to direct positively charged ions along a direction that is counter to the direction in which the ions are caused to drift as a result of ion-ion repulsion forces. The second electric field component is a longitudinal electric field that directs the ions along a direction that is approximately normal to the net ion trajectory through the analyzer region as a result of the carrier gas flow. The ions are directed by the second electric field component along a direction that is approximately perpendicular to the direction of radial focusing as a result of the applied CV and DV. Of course, the step of providing the second electric field component optionally includes a step of varying the positive dc potential that is applied to each one of the first outer electrode segment 64 and the third outer electrode segment 68, to obtain a maximum ion transmission efficiency. Alternatively, the positive dc potential is set to a predetermined value. Of course, a positive dc potential is applied in the case of positively charged selectively transmitted ions, whereas a negative dc potential is applied in the case of negatively charged selectively transmitted ions.

The electric fields for selectively transmitting ions through a FAIMS analyzer region are established optionally by applying an asymmetric waveform voltage and a dc compensation voltage to an outer electrode of the FAIMS, by applying an asymmetric waveform voltage and a dc compensation voltage to an inner electrode of the FAIMS, or by applying one of an asymmetric waveform voltage and a dc compensation voltage to one of an inner electrode and an outer electrode of the FAIMS and the other one of the asymmetric waveform voltage and the dc compensation voltage to the other one of the inner electrode and the outer electrode of the FAIMS. In the event that an asymmetric waveform voltage is being applied to a segmented electrode comprising a plurality of electrically isolated electrode segments, then it is necessary to separately apply a same asymmetric waveform voltage to each one of the plurality of electrode segments.

Numerous other embodiments may be envisaged without departing from the spirit and scope of the invention.

What is claimed is:

1. An apparatus for separating ions, comprising:
   an analyzer region defined by a space between first and second electrodes, the first electrode having a length and at least a quadratic ruled outer surface, the second electrode overlapping the first electrode along a first portion of the length thereof and having at least a quadratic ruled inner surface opposite to the at least a quadratic ruled outer surface of the first electrode;
   at least a first contact on at least one of the first and second electrodes for receiving a first direct current voltage, and for applying an asymmetric waveform voltage to the at least one of the first and second electrodes;
   a third electrode aligned with the second electrode for defining a space between the third electrode and the first electrode, the third electrode overlapping the first electrode along a second portion of the length thereof adjacent to the first portion of the length thereof and other than overlapping with the first portion of the length thereof; and,
   a second contact on the third electrode for at least one of receiving a second direct current voltage and applying the asymmetric waveform voltage to the third electrode,
   whereby during use the third electrode is maintained at a different potential relative to the second electrode, such that a potential gradient is formed in a direction along the length of the first electrode.

2. An apparatus according to claim 1, comprising an ion inlet orifice disposed within a first surface portion of the second electrode for introducing ions and a flow of a carrier gas into the analyzer region and an ion outlet orifice disposed within a second surface portion of the second electrode opposing the first surface portion for extracting ions from the analyzer region.

3. An apparatus according to claim 2, wherein during use the ions are selectively transmitted within the analyzer region between the ion inlet orifice and the ion outlet orifice along an average ion flow path absent a substantially linear portion, and wherein the ions are affected by the potential gradient such that ions within the average ion flow path are focused in a direction along the length of the first electrode and transverse to the average ion flow path.

4. An apparatus according to claim 2, comprising a control circuit for providing the potential difference between the second electrode and the third electrode of between 0 volts and 50 volts.

5. An apparatus according to claim 2, comprising a control circuit for providing the potential difference between the second electrode and the third electrode of between 0 volts and 2 volts.

6. An apparatus for separating ions, comprising:
an inner electrode having a length and an outer surface that is curved in a direction transverse to its length, and an outer electrode having a length, a channel through a portion thereof, and a curved inner surface, a portion of the length of the outer electrode overlapping a portion of the length of the inner electrode and forming an analyzer region therebetween, the outer electrode being approximately coaxially aligned with the inner electrode, the outer electrode including an ion inlet orifice and an ion outlet orifice defined one each within facing surface portions within the length of the outer electrode overlapping a portion of the length of the inner electrode, at least one of the inner and outer electrodes comprising a segmented electrode comprised of an electrode segment assembly, the electrode segment assembly including a plurality of electrode segments extending approximately a length coinciding with the length of the at least one of the inner and outer electrode, a surface of each of the electrode segments being opposite a surface of the other one of the inner and outer electrode;
at least a first contact on one of the other one of the inner and outer electrode and a first segment of the segmented electrode for receiving a first direct current voltage, and for applying an asymmetric waveform to the one of the other one of the inner and outer electrode and the first segment of the segmented electrode; and,
at least a second contact on a second segment of the segmented electrode for receiving a second direct current voltage, so as to form a potential gradient in a direction along the lengths of the inner and outer electrodes.

7. A method for separating ions, comprising the steps of:
providing an analyzer region defined by a space between first and second spaced apart electrodes;
introducing ions into the analyzer region;
providing a flow of a carrier gas through the analyzer region for directing the ions along a first direction within the analyzer region;
providing a first electric field component within the analyzer region resulting from the application of an asymmetric waveform voltage and a direct current compensation voltage to at least one of the first and second electrodes, for directing the ions along a second direction within the analyzer region that is approximately perpendicular to the first direction; and,
providing a second electric field component within the analyzer region for directing the ions along a third direction within the analyzer region, the third direction being approximately perpendicular to each one of the first direction and the second direction.

8. A method according to claim 7, including the step of applying a direct current voltage to third and fourth electrodes, such that a potential difference between the third electrode and the first electrode and a potential difference between the fourth electrode and the first electrode is different than a potential difference between the second electrode and the first electrode.

9. A method according to claim 7, including the step of varying the provided second electric field component so as to increase the ion transmission efficiency through the analyzer region.

10. A method for separating ions, comprising the steps of:
providing an analyzer region defined by a space between inner and outer electrodes having at least a quadratic ruled surface, the inner electrode having a length, the outer electrode overlapping the inner electrode along a potion of the length thereof;
transporting ions along an average ion flow path within the analyzer region, the average ion flow path extending in a first direction approximately transverse to the length of the inner electrode and absent a substantially linear portion the average ion flow path extending between an ion inlet orifice of the analyzer region and an ion outlet orifice of the analyzer region;
providing a radial electric field component within the analyzer region resulting from the application of an asymmetric waveform voltage and a direct current compensation voltage to at least one of the inner and outer electrodes for effecting a separation of the ions; and,
providing a longitudinal electric field component within the analyzer region for directing ions within the analyzer region in a second direction along the length of the inner electrode, the second direction being approximately perpendicular to the first direction.

11. An apparatus for separating ions, comprising:
an inner electrode and an outer electrode arranged in an overlapping coaxial arrangement so as to form an analyzer region therebetween;
at least a first contact on at least one of the inner electrode and the outer electrode for providing a first direct current voltage difference between the inner electrode and the outer electrode, and for applying an asymmetric waveform to at least one of the inner electrode and the outer electrode;
an ion inlet orifice within a first surface portion of the outer electrode for introducing ions into the analyzer region and an ion outlet orifice within a second surface portion of the outer electrode for extracting ions from the analyzer region, the first surface portion approximately facing the second surface portion;
wherein at least one of the inner electrode and the outer electrode comprises a segmented electrode comprising a first electrode segment having at least a second contact for providing a second direct current voltage potential difference between the first electrode segment and the other one of the inner electrode and the outer electrode.

12. An apparatus according to claim 11, comprising a second electrode segment, the first electrode segment and the second electrode segments being disposed such that the ion inlet orifice and the ion outlet orifice are between the first electrode segment and the second electrode segment, the second electrode segment comprising at least a third contact for providing a third direct current voltage difference between the second electrode segment and the other one of the inner electrode and the outer electrode.

13. An apparatus according to claim 12, comprising a control circuit for providing the second direct current voltage difference between the first electrode segment and the other one of the inner electrode and the outer electrode, and for providing the third direct current voltage difference between the second electrode segment and the other one of the inner electrode and the outer electrode, so as to establish potential gradients within the analyzer region for directing ions through the ion outlet orifice with an efficiency that is improved relative to an efficiency absent the potential gradients being established.

14. An apparatus according to claim 13, wherein during use the ions are selectively transmitted within the analyzer region between the ion inlet orifice and the ion outlet orifice along an average ion flow path absent a substantially linear portion, and wherein the ions are affected by the potential gradients such that ions within the average ion flow path are focused in a direction transverse to the average ion flow path.

15. An apparatus according to claim 11, wherein the inner electrode comprises the segmented electrode.

16. An apparatus according to claim 11, wherein the outer electrode comprises the segmented electrode.

17. An apparatus according to claim 16, wherein the inner electrode comprises a second segmented electrode.

18. An apparatus according to claim 11, wherein the inner electrode includes an outer surface that follows a curve defined by a quadratic ruled function.

19. An apparatus according to claim 18, wherein the quadratic ruled function defines a regular cylinder.

20. An apparatus according to claim 18, wherein the quadratic ruled function defines an elliptic cylinder.

21. An apparatus according to claim 11, wherein the outer electrode includes an inner surface that follows a curve defined by a quadratic ruled function.

22. An apparatus according to claim 21, wherein the quadratic ruled function defines a regular cylinder.

23. An apparatus according to claim 21, wherein the quadratic ruled function defines an elliptic cylinder.

* * * * *

UNITED STATES PATENT AND TRADEMARK OFFICE
CERTIFICATE OF CORRECTION

PATENT NO.       : 7,034,289 B2
APPLICATION NO.  : 10/503714
DATED            : April 25, 2006
INVENTOR(S)      : Guevremont et al.

Page 1 of 1

It is certified that error appears in the above-identified patent and that said Letters Patent is hereby corrected as shown below:

Claim 5, column 17, lines 20 / 21
replace "between 0 volts and 2 volts"
with --between 0 volts and 15 volts--

Signed and Sealed this

Tenth Day of March, 2009

JOHN DOLL
*Acting Director of the United States Patent and Trademark Office*